United States Patent [19]

Morris et al.

[11] Patent Number: 5,797,399
[45] Date of Patent: Aug. 25, 1998

[54] METHOD AND APPARATUS FOR IDENTIFYING AND CORRECTLY RESPONDING TO ABNORMAL HEART ACTIVITY

[75] Inventors: Milton M. Morris; Janice M. Jenkins; Lorenzo A. DiCarlo, all of Ann Arbor, Mich.

[73] Assignee: The Regents of the University of Michigan, Ann Arbor, Mich.

[21] Appl. No.: 639,859

[22] Filed: Apr. 19, 1996

[51] Int. Cl.$^6$ ............................................. A61B 5/0402
[52] U.S. Cl. ............................. 128/705; 607/5; 128/920
[58] Field of Search ............................... 128/696, 702, 128/705, 920; 607/4, 5; 364/413.06

[56] References Cited

PUBLICATIONS

Lorenzo A. DiCarlo, et al., "A Time–Domain Analysis of Intracardiac Electrograms for Arrhythmia Detection", *PACE*, vol. 14, pp. 329–336, Feb. 1991, Part II.

Lorenzo A. DiCarlo, et al., "Differentiation of Ventricular Tachycardia from Venticular Fibrillation Using Intraventricular Electrogram Morphology", *The American Journal of Cardiology*, vol. 70, pp. 820–822, Sep. 15, 1992.

Robert D. Throne, et al., "A Comparison of four New Time–Domain Techniques for Discriminating Monomorphic Ventricular Tachycradia from Sinus Rhythm Using Ventricular Waveform Morphology", *IEEE Transactions on Biomedical Engineering*, vol. 38, No. 6, Jun., 1991, pp. 561–570.

*Primary Examiner*—William E. Kamm
*Assistant Examiner*—Kennedy J. Schaetzle
*Attorney, Agent, or Firm*—Harness, Dickey & Pierce, P.L.C.

[57] ABSTRACT

A pattern recognition system for use in an implantable cardioverter defibrillator that is capable of responding correctively to abnormal activity of the heart efficiently and specifically. The system of the present invention first establishes a template standard defining a median or other statistical measure of central tendency representing the point above which or below which actual sample values would be remarkable. Against the median are compared sampled values within a window having a pre-programmed length. For each cycle, a comparison is made between the template median and every value sampled within this pre-programmed window. Each cycle is then individually diagnosed such that if a selected value is above a particular pre-established threshold or below a particular pre-established threshold it will be classified as abnormal. A plurality of specific cycles must be classified abnormal in order for a final diagnosis to be made that the individual is experiencing arrhythmia. The system of the present invention is also capable of differentiating between types of abnormal and can classify the abnormal as being either ventricular tachycardia and ventricular fibrillation.

36 Claims, 3 Drawing Sheets

METHOD AND APPARATUS FOR IDENTIFYING AND CORRECTLY RESPONDING TO ABNORMAL HEART ACTIVITY

SPONSORSHIP

The present invention was supported by the National Science Foundation grant Nos. EID-9018746 and GER-9023514 and a National Research Service Award No. 1F31GM17240-02 of the National Institute of General Medical Sciences (National Institutes of Health). The Government may have certain rights in this invention.

FIELD OF THE INVENTION

The present invention relates generally to signal detection and classification. More particularly, the present invention relates to a pattern recognition system for use in an implantable cardioverter defibrillator that is capable of responding correctively to abnormal activity of the heart efficiently and specifically.

BACKGROUND OF THE INVENTION

The heart may be viewed as a spontaneous current generator whose pumping action is effected by spontaneous generation of an electrical impulse (known as an action potential), conduction of the electrical impulse throughout the heart, and subsequent contraction of the heart muscle (myocardium) in response to the impulse. It is, therefore, electrical activity which initiates and controls muscular contraction of the heart.

Chemicals in the form of ions (such as sodium, potassium and chloride) reside in the extracellular and intracellular fluid of a muscle cell. The concentration gradients of these ions combined with cell membrane features make for a special ion arrangement at the inner and outer wall of the cell membrane. At rest, this special membrane arrangement produces a negative transmembrane potential. If the cell membrane is stimulated by an electrical impulse of adequate magnitude and proper polarity, a process known as an action potential will ensue. During an action potential a cell depolarizes (transmembrane potential becomes less negative) and then repolarizes (transmembrane potential returns to resting value). The impulse of adequate magnitude naturally comes from a neighboring cell undergoing an action potential. Thus, impulses are propagated through the heart via a cell-to-cell mechanism.

The heart's electrical impulse originates in the sino-atrial node and is transmitted (cell-to-cell) to all portions of the atria, resulting in the contraction of the atrial chambers. The electrical impulse continues in its path to reach a cluster of conduction fibrils known as the atrioventricular node, or the A-V node. By delaying conduction for approximately one-tenth of a second, the A-V node acts as a buffer for impulses from the atria to the ventricles. This allows for proper flow of blood from the atria to the ventricles.

Following this delay, the A-V node transmits an impulse that reaches another cluster of fibers known as the bundle of His which comprises left and right bundle branches of the His-Purkinjie system. The bundle branches terminate with the Purkinjie fibers which are themselves attached directly to the myocardial cells.

A coordinated wave of electrical impulses effects contraction of many myocardial cells simultaneously, thus causing the heart's pumping action. The action begins in the sino-atrial node from which impulses are provided spontaneously and periodically. The impulses travel to the surrounding cardiac tissue and propagate as a wave of depolarization. As noted above, contracting of the cardiac muscle of the atria follows after the depolarization. Subsequent ventricular conduction is initiated via the A-V node and the His-Purkinjie system.

Normal electrical function provides for continued proper functioning of the heart. However, aberrations in electrical origination or transmission produce concomitant malfunctions of the systemic delivery of blood to the body. The majority of cases of cardiac malfunction may be traced to a failure in the electrical conduction system of the heart. The result of such an electrical failure or change from the normal electrical activity and sequence of cardiac activity is an arrhythmia. Arrhythmias may be atrial, atrioventricular, or ventricular. Two of the most deadly forms of arrhythmia are ventricular tachycardia and ventricular fibrillation. Both of these events are generally defined as sustained ventricular arrhythmias.

In ventricular tachycardia, the sequence of ventricular extrasystoles occur at a rate of between 110 to 240 cycles per minute. This type of arrhythmia is characterized by atrioventricular dissociation, an abnormally wide QRS complex (surface lead electrodes), and a far more rapid rate than usual.

A sustained ventricular tachycardia may eventually lead to ventricular fibrillation in which the ventricular extrasystoles reach a frequency in excess of 330 cycles per minute. The condition brought about by this aberration in electrical conduction is an extremely dangerous and lethal arrhythmia.

Several methods are known to treat arrhythmia. Drugs are occasionally prescribed, and while having significant side effects, are often justified because of the severity of the arrhythmia. Drugs, called calcium antagonists, mediate the heart's conduction by halting electrical conduction by blocking the calcium channels of myocardial cells. Nitrates may be used as treatment in cases of acute myocardial infarction or congestive heart failure.

Another therapeutic technique is referred to as radio frequency ablation which is directed to neutralizing accessory electrically-conductive pathways of the heart which cause the heart to fail in properly conducting electrical impulses due to some small area of the heart which is skewing the direction of depolarization. In this technique, a catheter is introduced into the heart and a delivery of high frequency radio waves is used to burn away the faulty area of the heart. Following successful radio frequency ablation therapy, normal conduction of the heart will return and the particular arrhythmia associated with the damaged tissue will be eliminated.

One of the most common approaches to the elimination of arrhythmia is electrical therapy in which electrodes are fitted to either the body or the heart for selectively delivering an electrical current or shock to alter the rhythm of the heart. Implantable cardioverter defibrillators, or "ICDs", stimulate the heart directly using function generators with specific waveforms to respond to and treat arrhythmias on an "as-needed" basis.

Implantable cardioverter defibrillators have achieved overwhelming success in salvaging thousands of lives by providing immediate electrical therapy for the treatment of potentially lethal arrhythmias, i.e., ventricular tachycardia and ventricular fibrillation. These rhythms are believed responsible for over 80% of cases of sudden cardiac death, which claims 400,000 victims per year. The number of implants of ICDs is exceptional (over 75,000 implants to date), despite their relative infancy in the medical field.

A large remaining problem to be solved in ICD technology is refinement of detection criteria such that the device no longer offers a simple brute force solution (if in question, shock). This is a three-fold problem. First, false shocks are an unnecessary patient distress. Second, false shocks deplete battery power rendering the device less capable of addressing true urgencies and forcing premature explantation. Third, false delivery of therapy can initiate ventricular tachycardia (VT) or ventricular fibrillation (VF) when none previously existed.

In an effort to overcome these problems, present devices offer a multitude of therapies tailored to specific arrhythmias and provide a variety of programmable parameter settings. However, limitations in current detection capabilities remain, and the variety of selections has exacerbated rather than reduced the problem of excessive therapy. The present challenge is to optimize detection in order to direct appropriate therapy without sacrificing sensitivity of VT and VF detection, and without significantly increasing the complexity and power consumption in an implantable battery-operated device.

SUMMARY OF THE INVENTION

The present invention solves the problems referred to above by providing a morphologically based and non-parametric approach to arrhythmia classification. More particularly, the present invention defines a pattern recognition system for use in an implantable cardioverter defibrillator that is capable of responding correctively to abnormal activity of the heart efficiently and specifically. By first establishing a sample point representing a statistical measure of central tendency such as a median sample point of the ventricular depolarization and then comparing each sample against the median sample point, the present invention provides a method having specificity such that the probability is very high that a normal rhythm will be diagnosed as a normal rhythm. This minimizes the risk of misidentification of sinus rhythm. The method is also capable of differentiating between ventricular tachycardia and ventricular fibrillation.

At the heart of the present invention is a pattern recognition system. The signal representing an intracardiac electrogram is passed through a filter to a sampler. The sampler produces a digitized signal which is delivered for feature selection into a selector. A variety of feature selections are possible. For example, the produced data may or may not be put through orthogonal transformation or a similar transformation, or may be subject to dimensionality reduction or similar compression.

The feature selector outputs the selected features to a trained classifier which may be formed to provide information as to what group the produced signal should be clustered. For example, the classifier may determine that the signal should be clustered with ventricular tachycardia. The classifier thereafter outputs the classified information so that a therapeutic decision may be made.

According to the method of the present invention, a heart cycle template defining a statistical measure of central tendency such as a median is initially determined representing the point above which or below which actual sample values would be remarkable. A window having a preprogrammed length is also established for processing the signals. For each cycle, a comparison is made between the template median and every value sampled within this preprogrammed window. The number of times the difference between the sample value and the median is greater than "0" is represented by the value "K" which corresponds to the count or the number of samples that are actually above the median. Every time the sample value is determined to be greater than the median, a K-counter is incremented by 1. If the sample value is not greater than the median, the K-counter retains the current value. This way, K can be as little as 0 and as much as the window length.

The final value for K, arrived at after the last sample within the window is processed, is compared to two thresholds, $\gamma_1$ and $\gamma_2$, and a cycle diagnosis is made. Each cycle is individually diagnosed such that if K is above a particular pre-established threshold or below a particular pre-established threshold it will be classified as abnormal. A plurality of specific cycles must be classified abnormal in order for a final diagnosis to be made that the individual is experiencing arrhythmia. By using an X-of-Y analysis to buffer the final diagnosis from the collected cycle-by-cycle diagnoses (where, taken individually, errors may occur), control of the level of sensitivity and specificity in the classification of rhythms is achieved. The result of this analysis is a diagnosis of sinus rhythm or abnormal rhythm. If the result of the X-count divided by the number of heart beats (cycles–analyzed Y) is less than a pre-programmed threshold $\gamma_3$, the diagnosis for the last Y cycles is abnormal. The only alternative is a finding of sinus rhythm.

Once it is established that abnormality exists, further analysis is undertaken to determine if function(s) and/or transformation(s) of the K-counts meet a preselected criterion. If they do, then the signal being analyzed is an element of a particular class of signals. The count analysis tool is used to further classify rhythms diagnosed as abnormal into sub-categories, including ventricular tachycardia or ventricular fibrillation. It may also be used to catch non-lethal rhythms such as sinus tachycardia (ST) or supraventricular tachycardia (SVT). The appropriate therapy may thus be delivered and false positives may thus be avoided.

DETAILED DESCRIPTION OF THE INVENTION

The present invention relates to an implantable cardioverter defibrillator that incorporates a non-parametric approach to arrhythmia classification. By first establishing a sample point representing a statistical measure of central tendency such as a template median and then comparing each sample against the median template, the present invention provides a method having specificity such that the probability is very high that a normal rhythm will be diagnosed as a normal rhythm, thus reducing the risk of misdiagnosing normal rhythms as abnormal rhythms. The method of the present invention is also sensitive enough to differentiate sinus rhythm from ventricular tachycardia and ventricular fibrillation and differentiate ventricular tachycardia from ventricular fibrillation. It is also to be understood that all steps mentioned in this detailed description may be accomplished using software, hardware (either digital or analog or a combination of both) or firmware or a combination of any two or three of software, hardware and firmware.

Figure 1:
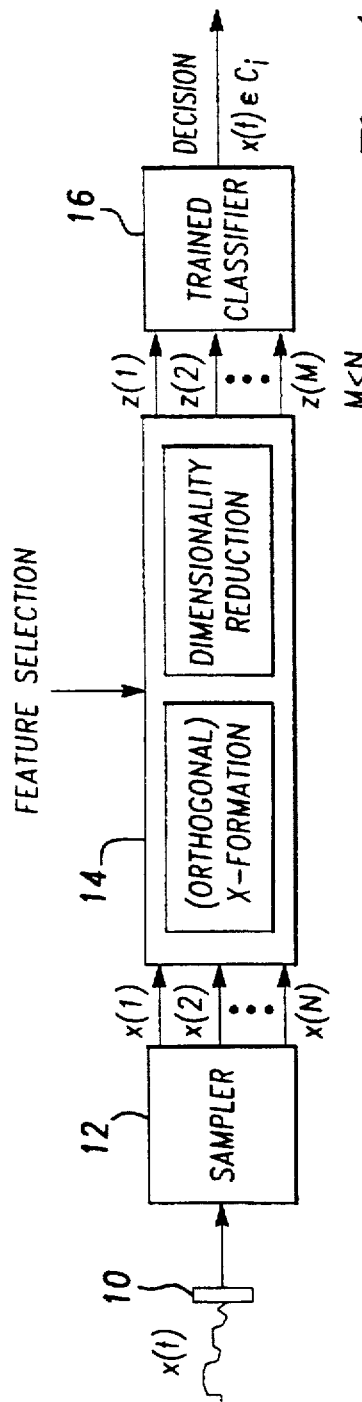
FIG. 1 is a diagrammatic representation of a pattern recognition system used to develop the present invention.

To accomplish this end, the present invention was developed using a pattern recognition system broadly shown in FIG. 1. A signal x(t) which is the intracardiac electrogram is passed through a filter 10 as it is delivered to a sampler 12 at a preselected sampling rate. The sampler 12 produces a digitized signal (x(1), x(2), . . . x(N)) which is delivered for feature selection into a selector, generally illustrated as 14. At this stage the data may or may not be put through orthogonal transformation or a similar transformation. The data further may be subject to dimensionality reduction or similar compression. These features of the input x(1), x(2), . . . x(N) selected by the feature selector 14 for classification are only exemplary and other features may be selected in addition or in the alternative.

The feature selector 14 outputs the selected features (z(1), z(2), . . . z(M)) where M is less than or equal to (N) to a trained classifier 16. The classifier may be formed to provide information as to what group the signal x(t) should be clustered, for example, whether or not the determined x(t) can be clustered with ventricular tachycardia. The classifier 16 thereafter outputs the classified information so that a decision may be made. The pattern recognition system described with respect to FIG. 1 is used according to the present invention to gather samples above the template median. (The median as used herein is illustrative. Because the performance of the altered algorithm could be negatively or positively affected depending on the patient which the algorithm will service, this value could well be any statistical measure of a central tendency as mentioned above.)

Figure 2:
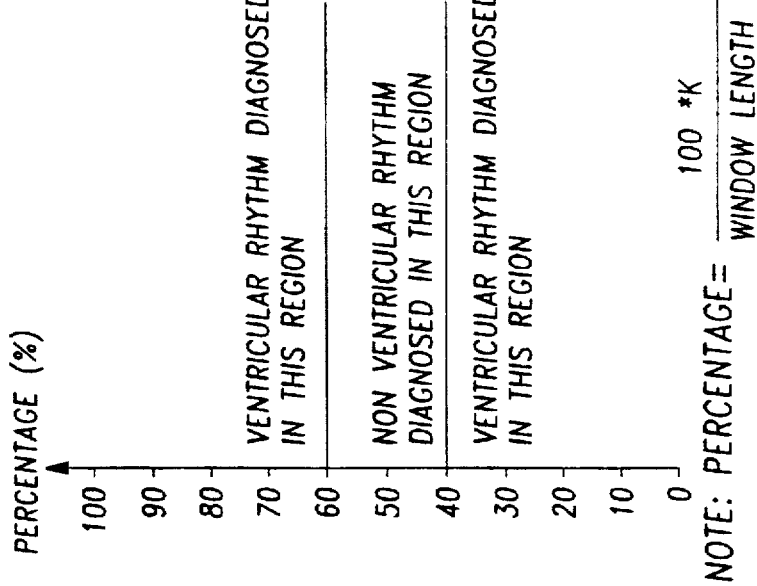
FIG. 2 is a graphical representation of the mathematical formulations used for signal classification.

FIG. 2 illustrates an example of a graphical representation of the mathematics used for signal classification in the signal classifier 16. According to this example, sinus rhythm (SR) is defined between 40% and 60%, while ventricular tachycardia is recognized as being above 60% and below 40%. (In FIG. 2, "K" corresponds to a count or a number of samples actually above the median and $\gamma_{1,2}$ represent the threshold values for class boundaries.) It is to be understood that while these particular percentages (40% and 60%) were defined by the example, other percentage values may be used to define sinus rhythm and abnormality in other examples.

Figure 3:
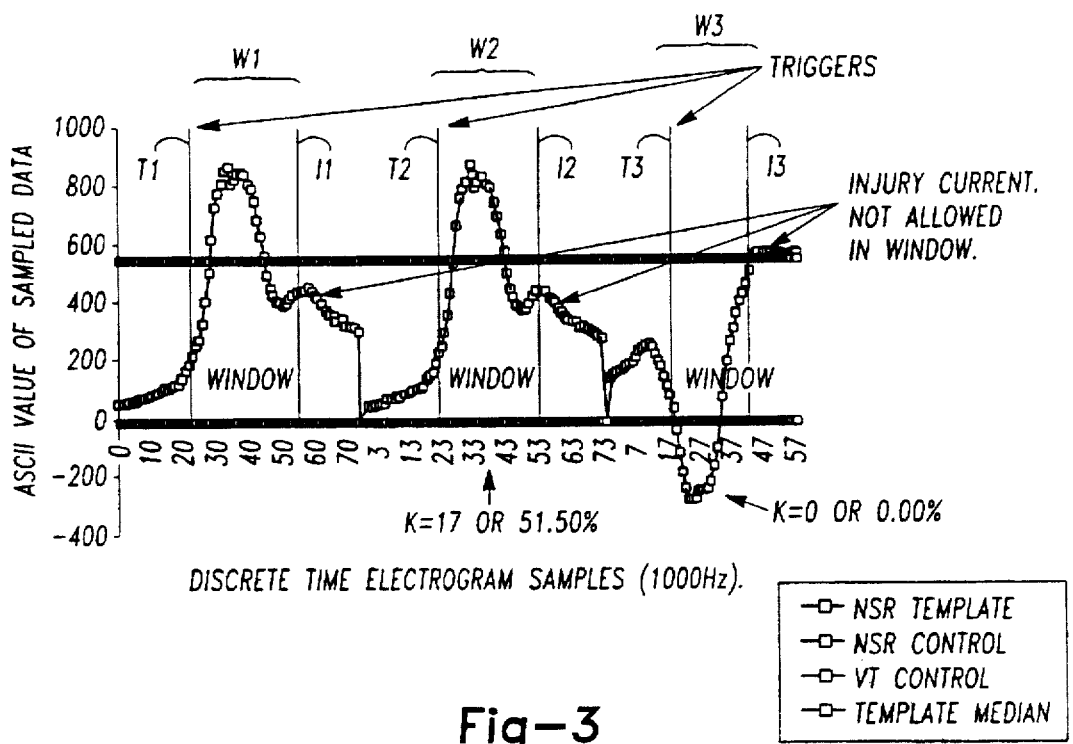
FIG. 3 is a graphical representation of the various waveforms which can be classified using the present method.

FIG. 3 illustrates an example of a patient diagnosed using samples above the median (the presented method). On the Y-axis are located sampled data points ranging from data point one to 73.

There are three windows illustrated in the sample diagnosis labeled W1, W2, and W3. Each window "opens" at its respective fiduciary point (T1, T2, T3). Each window "closes" based on a user-specified criterion. The criterion may be based on some set window length that does not change or the criterion may be based on some adjusting window length. Any method of closing the window may be used. However, algorithm robustness will be effected adversely or positively depending on the determination of window length.

The critical aspect is not the particular window length itself, but rather that the same method for finding window length be used consistently throughout the data gathering steps. The window length is defined by each pair of vertical lines T1-I1, T2-I2, T3-I3. The window length as well as values for $\gamma_{1,2}$ are preselected at the time the ICD is implanted according to the particular patient data collected during electrophysiology studies.

To arrive at the sample diagnoses represented in FIG. 3, data were analog filtered at 1–500 Hz and sampled at 1000 Hz (a sampling of 1000 points every second). After acquisition, data were transformed to "*.sig" format (a storage format created in the Medical Computing Laboratory of the University of Michigan, Ann Arbor) and truncated to 16 cycles and stored on a computer hard drive for processing. During processing, data were converted from "*.sig" format to ASCII.

Several cycles were accounted for when estimating the window length and set such that ventricular depolarization falls within the window. Each cycle is isolated using the fiduciary location combined with a priori knowledge of window lengths. Each cycle represents a heart beat. The individual cycles are isolated using an auto-adjusting gain fiduciary and window length (in points).

Each block in FIG. 3 represents a discrete sample, the "K" corresponding to the count or the number of samples that are actually above the template median, shown as a horizontal solid black line. For the subsequent passages of SR and VT (which are to be classified), each cycle was extracted from the ASCII file and data was compared to a predetermined median value.

Sinus rhythm is monomorphic, having a single morphology. Accordingly, each cycle is virtually identical to the previous cycle. Ventricular tachycardia may be either monomorphic or polymorphic. (Polymorphic ventricular tachycardia is faster than its monomorphic form and generally requires a higher energy shock to resolve.)

For each cycle, a comparison is made between the template median and the sampled values within the window. If the value is greater than the median, the K-counter is incremented by 1. Otherwise, K keeps the current value. This way, K can be as little as 0 and as much as the window length. This stage of the algorithm is called "sign-detection" because the K counted is actually the number of times the difference between the sample value and the template median $(r_i-m_{temp})$ is greater than 0 (or carries a positive sign). The sampling rate of the sample shown in FIG. 3 is 1000 Hz, therefore, each point represents a msec of time. The final K value, arrived at after the last sample within the window is processed, is compared to two thresholds, $\gamma_1$ and $\gamma_2$, and a cycle diagnosis is made.

Accordingly, with the K-counter the illustrated percentage may be created to form the illustrated vertical graph of percentages. Thresholds may thereafter be established between which diagnosis of either normal or abnormal rhythm would be established. A signal diagnosed as either above or below the thresholds which define the sinus rhythm zone is diagnosed as abnormal. The illustrated percentage defines ventricular tachycardia, although other abnormal rhythms could as well be used. For example, ventricular fibrillation could be demonstrated.

Once the median is derived (where 50% of the data is above the median point and 50% is below), the median value is compared against every sample within the window to this median. A counter is increased every time a sample is above the median. In the graph of FIG. 3, the sample was above the median 17 times or 51.5%. This finding is consistent with what would be expected a number somewhere near 50% for sinus rhythm. Conversely, a figure illustrative of ventricular tachycardia would be significantly different from the 50% range, either higher or lower. The last window, W3, the ventricular tachycardia control, illustrates that no samples appear above the median line, thus resulting in a K-count of zero or 0%.

The shape of the ventricular tachycardia represented in window W3 of FIG. 3 is only exemplary, and other shape representations of ventricular tachycardia are possible. If an individual exhibits multiple tachycardias, the waveform for each may be unique. Accordingly, the waveform of FIG. 3 is intended as being exemplary and not limiting.

As briefly noted above, the next stage is a simple X-of-Y classifier. In the particular example, each cycle has the K-counter associated therewith. However, each cycle is individually diagnosed such that if K is above a particular threshold or below a particular threshold it will be classified as abnormal. A plurality of the last Y cycles must be classified abnormal in order for a final diagnosis to be made that the individual is experiencing arrhythmia. A variety of criteria may be used for this determination. In the present illustration, a 75% criteria is employed. (Other criteria, such as 50% or 25%, may also be used.) If the index of the evaluated samples is large enough to meet the preselected criteria, therapy is delivered. The X-of-Y analysis accordingly helps to avoid false positives. Using the present illustration, the X-counter is incremented by 1 for every cycle which is classified as VT. If 12 of the last 16 cycles (75%) is diagnosed as VT, the final diagnosis is VT and a recommendation or call for therapy is made.

Figure 4:
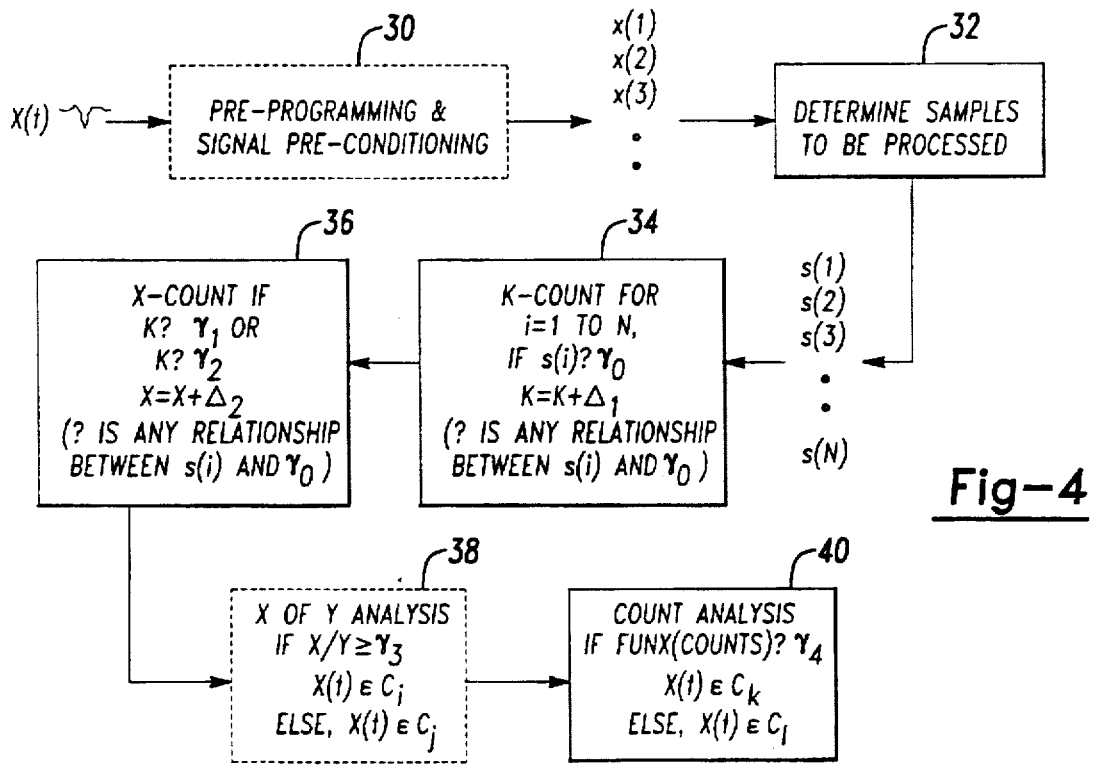
FIG. 4 is a general overview of the steps involved in signal detection and classification according to the present invention.
Figure 5:
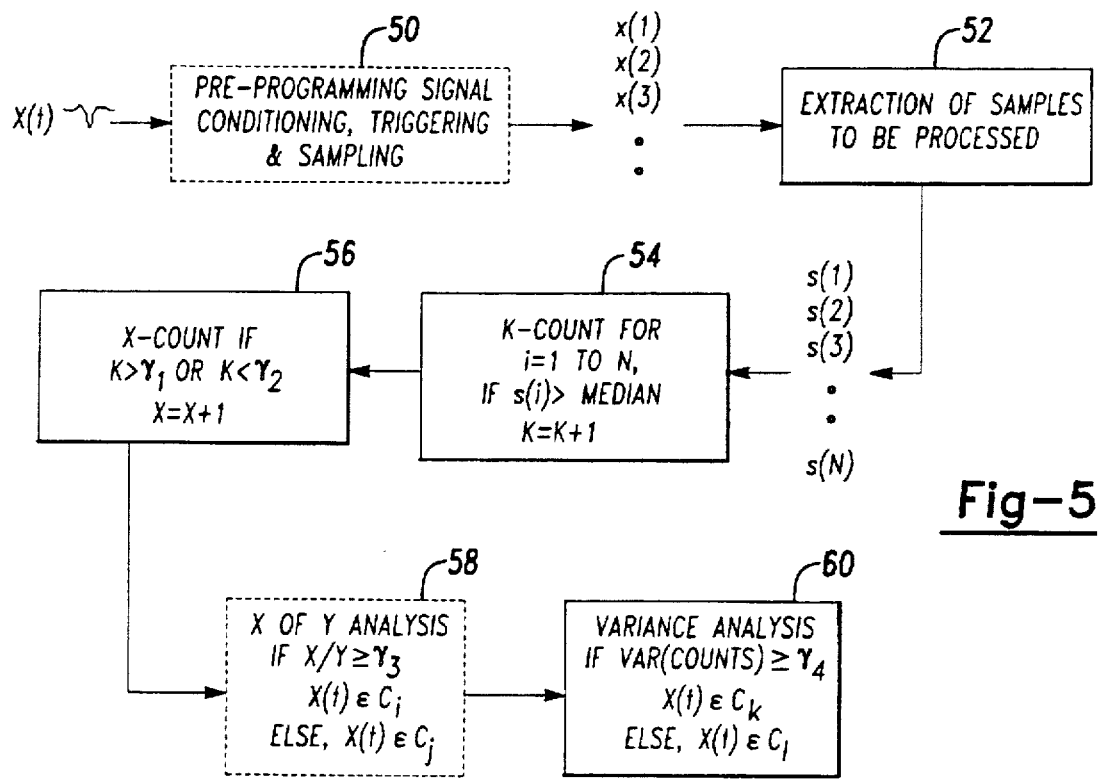
FIG. 5 is a stepwise overview similar to that of FIG. 4, but illustrating specialized steps of classification.

Further understanding of the present invention may be had by reference to FIGS. 4 and 5 which are block diagrams illustrating the step-by-step analysis and interpretation of a patient's intracardiac electrocardiogram signals.

With reference to FIG. 4, a general overview of the steps involved in signal detection and classification according to the present invention is illustrated. The input data x(t) represents any signal or portion of a signal, or transformation of a signal, or feature of a signal representative of some biological mechanism or any cardiovascular element such as the heart including the heart muscle.

Step 30 represents the pre-programming and signal pre-conditioning of an ICD undertaken at the time of implantation by the cardiologist. In this step, the preprogramming involves the fine-tuning of the ICD to the individual based on known data. The sampling portion of this step involves the extraction of a "sample" from data frequently and at regular intervals of time. This component of Step 30 is important because computer chips operate on digitized (sampled) data and not on analog (continuous) data. Step 30 produces signals x(1), x(2), x(3) . . . x(N).

Step 32 is the step at which the samples to be processed are determined. This data set will be further processed to determine to what signal class ($C_?$) a given heart beat belongs. Step 32 produces signals s(1), s(2), s(3) . . . s(N).

Step 34 involves the K-count which is an index which changes by $\Delta_1$ when a sample value or certain number of sample values is of some relation to a threshold $\gamma_0$. Typical relations are greater than (>), greater than or equal ($\geq$), equal (=), less than or equal ($\leq$), or less than (<).

Step 36 involves the X-count which is an index which changes by $\Delta_2$ when a K-count or a certain number of K-counts is of some relation to a threshold $\gamma_1$ or is of some relation to another threshold $\gamma_2$. Typical relations are greater than (>), greater than or equal ($\geq$), equal (=), less than or equal ($\leq$), or less than (<).

Step 38 is the step at which the X-of-Y analysis occurs. The X-of-Y analysis is used to buffer the final diagnosis from cycle-by-cycle diagnoses where errors may occur. This allows for control of the level of sensitivity and specificity in the classification of rhythms. The result of this box is a diagnosis of sinus rhythm or abnormal rhythm. If the result of the X-count divided by the number of heart beats (cycles–analyzed Y) is less than a pre-programmed threshold $\gamma_3$, the diagnosis for the last Y cycles is abnormal. The only alternative is a finding of sinus rhythm.

Step 40 is the count analysis step. In this step, if function (s) and/or transformation(s) of the K-counts meet a preselected criterion, then the signal being analyzed is an element of a particular class of signals. The count analysis tool is used to further classify rhythms diagnosed as abnormal into sub-categories, including ventricular tachycardia or ventricular fibrillation. As discussed above, these two rhythms are both potentially lethal (particularly the latter state) but do not require the same electrical therapy. (In effect, this step could be taken prior to Step 38.) This step may also be used to catch non-lethal rhythms such as sinus tachycardia (ST) or supraventricular tachycardia (SVT).

With reference to FIG. 5, an overview of more specialized steps involved in signal detection and classification according to the present invention is illustrated. This figure is provided to illustrate the versatility of the described method.

As with the diagram of FIG. 4, the input data x(t) of FIG. 5 represents any signal or portion of a signal, or transformation of a signal, or feature of a signal representative of some biological mechanism or any cardiovascular element such as the heart including the heart muscle.

Step 50 involves the substeps of pre-programming, signal conditioning, triggering, and sampling. Conditioning may take on various forms such as filtering signals, differentiating signals, or even normalizing signals.

The substep of triggering refers to event marking. The event in the present case is a heart beat, or the depolarization and subsequent repolarization of the myocardium. This substep is part of isolating the necessary data used for processing.

The substep of sampling is used for referring to the extraction of a "sample" from the data frequently and at regular intervals of time. This is necessary because computer chips operate on digitized (sampled) data and not on analog (continuous) data, as set forth in Step 30 of FIG. 5 above.

Step 50 produces signals x(1), x(2), x(3) . . . x(N).

Step 52 provides for the extraction of samples to be processed. The necessary data for processing may be extracted from a digitized signal. The window length, part of the information that may be pre-programmed, determines the number of samples to be extracted. (Alternatively, the window length may be automatically determined and adjustable from cycle to cycle.) This extraction of samples starts at the fiduciary point and continues until the number of samples extracted equals the window length. Step 52 results in a data set (s(1), s(2), s(3) . . . s(N)) length equal to the pre-programmed window length. This data set will be further processed to determine to what signal class ($C_?$) this particular heart beat belongs.

Step 54 involves the K-count which is an index that increments by 1 each time a sample value is greater than the median value.

Step 56 involves the X-count which is an index that increments by 1 each time a K-count is greater than a preprogrammed threshold $\gamma_1$ or is less than a preprogrammed threshold $\gamma_2$.

Step 58, as with Step 38 described above with respect to FIG. 4, is the step at which the X-of-Y analysis occurs. The X-of-Y analysis is used to buffer the final diagnosis from cycle-by-cycle diagnoses where errors may occur. This allows for greater accuracy (higher specificity) in the classification of rhythms. The result of this box is a diagnosis of sinus rhythm or abnormal rhythm. If the result of the X-count divided by the number of heart beats (cycles-analyzed Y) is less than a pre-programmed threshold $\gamma_3$, the diagnosis for the last Y cycles is abnormal. The only alternative is a finding of sinus rhythm.

Step 60 is the variance analysis. The variance analysis tool is used to further classify rhythms diagnosed as abnormal into sub-categories such as ventricular tachycardia or ventricular fibrillation. As noted above, these two rhythms are both lethal, but do not require the same electrical therapy. Step 60 could precede Step 58.

In order that this invention may be better understood, the following examples are set forth. These examples are for purposes of illustration only, and are not to be construed as limiting the scope of the invention in any manner.

EXAMPLES

A simulator analysis intended to mimic the pattern recognition system of the present invention was made using MATLAB™ software. The analysis was configured to define particular parameters. A variety of such parameters are possible and include variations directed to the number of episodes to be classified, the number of heart cycles to be analyzed in the episode, the "X" and the "Y" of the X-of-Y analysis, the window length for processing each of the above-described three signals (together with the template passage), the sampling rate, the use of a filter, and the methods used for triggering on the collected data.

Figure 6:
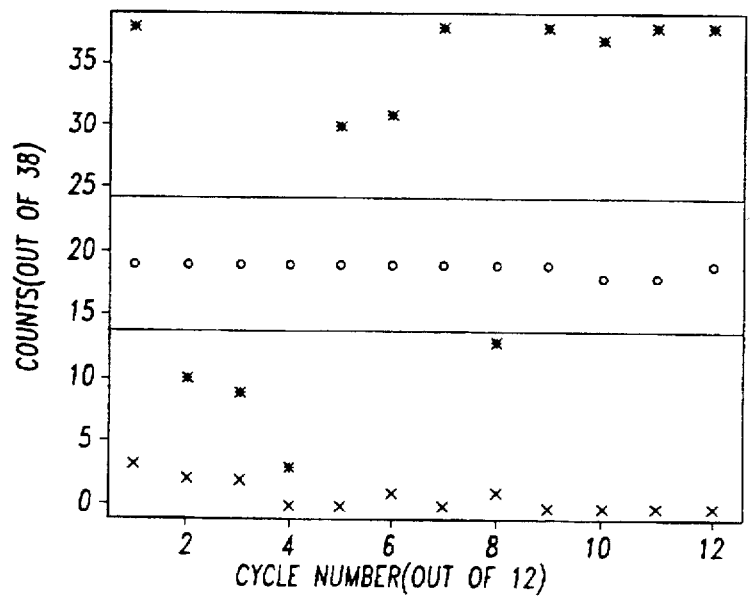
FIG. 6 is a graph representing the number of data points above the median for each heart cycle according to the examples achieved using the method of the present invention; and Table 1 illustrates a sample diagnosis according to the present method.

Table 1 illustrates a sample diagnosis according to the present method. "Count" refers to a number of samples above the median. FIG. 6 relates to Table 1 and graphically represents the number of data points identified as being above the median for each cycle. Window length was set at 38 msec which translates into 38 samples (sampling rate of 1000 Hz). Accordingly, each K-count is out of 38 and the Y-axis represents counts. This indicates the number of samples above the median. The X-axis defines cycle numbers 1 through 12.

Three rhythms were used in the sample. Later review shows that each rhythm was correctly diagnosed. The "diagnosis" of Signal 1 as indicated by circles represents sinus rhythm. The "diagnosis" of Signal 2 is indicated by "x's", while "diagnosis" of Signal 3 is indicated by stars. As would be expected, sinus rhythm generally hovers around 19 or 50% of the window length.

As is shown, the Signals 2 and 3 are beyond the thresholds for the sinus rhythm, which is defined by an upper limit of 24 and a lower limit of 14. Thus the Signals 2 and 3 provide a diagnosis of abnormality.

The values indicated by Signals 2 and 3 are further classified in Table 1 to determine the type of abnormal rhythm. Specifically, a variance of the counts was taken for each rhythm to show its potential in further separating ventricular tachycardia (VT) from ventricular fibrillation (VF).

Based on the variance analysis, Signal 2 identifies ventricular tachycardia. Signal 3 identifies ventricular fibrillation. As illustrated, the values indicating ventricular fibrillation are sometimes below or above the region representing sinus rhythm. This illustrates the characteristic chaotic signal produced by ventricular fibrillation. This fact compares well with the statistically consistent appearance of ventricular tachycardia. Because the variance expected for ventricular fibrillation is great relatively speaking when compared to to ventricular tachycardia, the two abnormality states may be easily differentiated from each other.

The present method offers significant improvements over known methods of tachycardia recognition in implantable cardioverter defibrillators. For example, because the ICDs are devices which are small, battery space and power are limited. By making the algorithm as simple as possible as has been done in the present invention, only a few energy-consuming counters and comparators are necessary. Furthermore, the method of the present invention demonstrates considerable specificity, thereby minimizing misdiagnoses and the consequent wastage of battery power.

Importantly, the data necessary to tune an ICD to follow the above-described method is the same as that already produced from conventional electrophysiology studies. Accordingly, the implanting surgeon need not adopt a different assessment procedure to prepare and install an ICD formed along the outline of the present invention.

TABLE 1

| PERFORM X OF Y DIAGNOSIS |
| --- |
| NUMBER OF CYCLES ANALYZED IS |
| 12 |
| WINDOW LENGTH IS |
| 38 |
| THRESHOLDS FOR K-COUNTS ARE |
| 24 & 14 |
| ##### SIGNAL 1 ##### |
| k_counts=19 19 19 19 19 19 19 19 19 18 18 19 |
| DIAGNOSIS= SINUS RHYTHM |
| ##### SIGNAL 2 ##### |
| k_counts+3 2 2 0 0 1 0 1 0 0 0 0 |
| DIAGNOSIS= DISEASED |
| ##### SIGNAL 3 ##### |
| k_counts=38 10 9 3 30 31 38 13 38 37 38 38 |
| DIAGNOSIS= DISEASED |
| VARIANCE ANALYSIS FOR FURTHER CLASSIFICATION OF DISEASED RHYTHMS |
| VARIANCE THRESHOLD IS |
| 100 |
| ##### SIGNAL 2 ##### |
| var_sign2=1.1136 |
| DIAGNOSIS= SIGNAL 2 IS VENTRICULAR TACHYCARDIA |
| ##### SIGNAL 3 ##### |
| var_sign= 192.2652 |
| DIAGNOSIS= SIGNAL 3 IS VENTRICULAR FIBRILLATION |

We claim:

1. A method for correctively responding to abnormal activity of a heart, the method including the steps of:

establishing a desired heart depolarization cycle template standard defining a statistical measure of central tendency;

determining a window having a length;

establishing a abnormality threshold;

monitoring the heart to identify heart depolarization samples within said determined window;

comparing said template standard and said samples within said determined window to determine the number of said samples that are beyond said standard;

establishing a counter value equal to a number of said samples that are beyond said standard;

diagnosing a cycle as to whether or not abnormality is present by comparing said sample value with said abnormality threshold; and correctively responding if abnormal activity is diagnosed.

2. The method for correctively responding to abnormal activity of the heart according to claim 1, further including the step of establishing a first abnormality threshold and a second abnormality threshold.

3. The method for correctively responding to abnormal activity of the heart according to claim 2, further including the step of diagnosing a cycle as to whether or not abnormality is present by comparing said counter value with said first and second thresholds.

4. The method for correctively responding to abnormal activity of a heart according to claim 1, further including the step of identifying arrhythmia based on at least two diagnosed cycles.

5. The method for correctively responding to abnormal activity of a heart according to claim 4, further including the step of collecting a plurality of counter values.

6. The method for correctively responding to abnormal activity of a heart according to claim 5, further including the step of determining a third threshold, dividing said collected counter values by the total number of heart cycles to buffer the final diagnosis to produce an X-of-Y value, and comparing said X-of-Y value with said third threshold to identify abnormality.

7. The method for correctively responding to abnormal activity of a heart according to claim 1, further including the step of conducting a variance analysis of the counter values to classify the identified abnormality as a particular kind of abnormality.

8. The method for correctively responding to abnormal activity of a heart according to claim 1, further including the step of classifying the identified abnormality as being ventricular tachycardia or ventricular fibrillation.

9. The method for correctively responding to abnormal activity of a heart according to claim 1, further including the step of using a defibrillator to perform the steps of identifying heart rate samples within said determined window, determining the number of said samples that are beyond said value defining a statistical measure of central tendency, classifying said determined number of samples beyond said value as a counter value, and diagnosing a cycle as to whether or not abnormality is present.

10. The method for correctively responding to abnormal activity of the heart according to claim 1, wherein at least one of the steps is accomplished using computer software.

11. The method for correctively responding to abnormal activity of the heart according to claim 1, wherein at least one of the steps is accomplished using computer hardware.

12. The method for correctively responding to abnormal activity of the heart according to claim 1, wherein at least one of the steps is accomplished using computer firmware.

13. The method for correctively responding to abnormal activity of the heart according to claim 1, further including the step of producing a sampler signal based on said heart depolarization samples.

14. The method for correctively responding to abnormal activity of the heart according to claim 13, wherein the step of producing said sampler signal includes the step of producing a digitized sampler signal.

15. The method for correctively responding to abnormal activity of the heart according to claim 13, wherein the step of producing said sampler signal includes the step of producing an analog sampler signal.

16. The method for correctively responding to abnormal activity of the heart according to claim 1, wherein the step of establishing a desired heart depolarization cycle template standard defining a statistical measure of central tendency includes the step of establishing a desired heart depolarization cycle template median.

17. A method for correctively responding to abnormal activity of a heart, the method comprising the steps of:

delivering a signal representing an intracardiac electrogram to a sampler;

effecting said sampler to produce a sampler signal;

providing said sampler signal to a feature selector to select a particular featured signal;

selecting at least one featured signal;

providing one or more of said selected featured signals to a classifier;

classifying the selected featured signal as representing either sinus rhythm or abnormality, the step of classifying the selected featured signal including the steps of:
identifying a template standard representing a statistical measure of central tendency;
identifying a threshold;
producing a counter value by identifying the number of samples outside said template standard; and
correctively responding if an abnormality is classified.

18. The method for correctively responding to abnormal activity of a heart according to claim 17, further including the step of causing the signal delivered to said selector to be put through orthogonal transformation.

19. The method for correctively responding to abnormal activity of a heart according to claim 18, further including the step of subjecting the transformed data to dimensional reduction.

20. The method for correctively responding to abnormal activity of a heart according to claim 17, further including the step of passing said signal through a filter before it is delivered to said sampler.

21. The method for correctively responding to abnormal activity of a heart according to claim 17, including the step of classifying the selected featured signal as being abnormal or non-abnormal based on a comparison of said sample value with said threshold.

22. The method for correctively responding to abnormal activity of a heart according to claim 21, including the step of identifying a second threshold.

23. The method for correctively responding to abnormal activity of a heart according to claim 22, including the step of classifying the selected featured signal as being abnormal or non-abnormal based on a comparison of said counter value with said threshold and said second threshold.

24. The method for correctively responding to abnormal activity of a heart according to claim 17, including the step of identifying a counter window and determining said counter value based on samples taken from within said sample window.

25. The method for correctively responding to abnormal activity of a heart according to claim 17, including the steps of collecting a plurality of counter values and conducting a variance analysis of the counter values to classify the abnormal sinus rhythm.

26. The method for correctively responding to abnormal activity of a heart according to claim 17, including the step of classifying the abnormal sinus rhythm as being ventricular tachycardia or ventricular fibrillation.

27. The method for correctively responding to abnormal activity of a heart according to claim 17, wherein the step of effecting said sampler to produce a sampler signal includes the step of producing a digitized sampler signal.

28. The method for correctively responding to abnormal activity of a heart according to claim 17, wherein the step of effecting said sampler to produce a sampler signal includes the step of producing an analog sampler signal.

29. A system for correctively responding to abnormal activity of the heart, the system comprising:

a sampler portion for receiving an intracardiac electrogram signal and for producing a sampler signal including a plurality of signals;

a feature selector portion for selecting a particular featured signal based on said sampler signal;

means for delivering said sampler signal to said feature selector;

a classifier portion for classifying said selected featured signal as representing either sinus rhythm or abnormality;

means for delivering said selected featured signal to said classifier means for producing a template standard;

means for identifying a threshold;

means for producing a counter value based on identification of the number of samples outside said template standard; and means, responsive to said classifier portion, for correctively responding to an abnormality.

30. The system for correctively responding to abnormal activity of the heart according to claim 29, including a filter operatively associated with said sampler portion.

31. The system for correctively responding to abnormal activity of the heart according to claim 29, wherein said classifier portion includes means for comparing said counter value with said threshold for classifying said selected featured signal as being abnormal or non-diseased.

32. The system for correctively responding to abnormal activity of the heart according to claim 31, including means for identifying a second threshold.

33. The system for correctively responding to abnormal activity of the heart according to claim 32, wherein said classifier portion includes means for comparing said counter value with said threshold and said second threshold for classifying said selected featured signal as being abnormal or non-diseased.

34. The system for correctively responding to abnormal activity of the heart according to claim 33, further including means for identifying a counter window and for determining said counter value on samples taken from within said counter window.

35. The system for correctively responding to abnormal activity of the heart according to claim 29, wherein said classifier further comprises means for conducting a variance analysis of a plurality of counter values to classify said abnormal sinus rhythm.

36. The system for correctively responding to abnormal activity of the heart according to claim 29, wherein said classifier portion includes means for classifying said abnormal sinus rhythm as being ventricular tachycardia or ventricular fibrillation.

\* \* \* \* \*

UNITED STATES PATENT AND TRADEMARK OFFICE
CERTIFICATE OF CORRECTION

PATENT NO. : 5,797,399                       Page 1 of 2

DATED        : August 25, 1998

INVENTOR(S) : Milton M. Morris; Janice M. Jenkins; and Lorenzo A. DiCarlo

It is certified that error appears in the above-identified patent and that said Letters Patent is hereby corrected as shown below:

ON THE TITLE PAGE, under References Cited,

--U.S. Patent Documents

| | | | |
|---|---|---|---|
| 5,542,430 | 8/1996 | Farrugia et al. | 128/705 |
| 5,447,519 | 9/1995 | Peterson | 128/705 |
| 5,311,874 | 5/1994 | Baumann et al. | 128/702 |
| 5,271,411 | 12/1993 | Ripley et al. | 364/413.06 |
| 5,240,009 | 8/1993 | Williams | 364/413.06 |
| 5,217,021 | 6/1993 | Steinhaus et al. | 128/705 |
| 4,680,708 | 7/1987 | Ambos et al. | 128/705 |
| 4,492,235 | 1/1985 | Sitrick | 128/705-- . |

Abstract, line 21
    (Amendment dated 4/22/97, page 2, lines 4-5)
       both occurrences of "abnormal" should be --abnormality--.

Column 1, line 8 delete 2nd occurrence of "the".

Column 7, line 2 after "expected" insert a hyphen.

UNITED STATES PATENT AND TRADEMARK OFFICE
CERTIFICATE OF CORRECTION

PATENT NO. : 5,797,399

DATED : August 25, 1998

INVENTOR(S) : Milton M. Morris; Janice M. Jenkins; and Lorenzo A. DiCarlo

It is certified that error appears in the above-identified patent and that said Letters Patent is hereby corrected as shown below:

Column 9, line 52 delete " "x's" " and substitute --"x"s--.

Column 10, line 60, claim 1 delete "a" and substitute --an-- therefor.

Column 12, line 40, claim 21

"sample" should be --counter--.

Signed and Sealed this

Second Day of May, 2000

Attest:

Q. TODD DICKINSON

Attesting Officer      Director of Patents and Trademarks